United States Patent
Del Rio et al.

[11] Patent Number: 5,494,359
[45] Date of Patent: Feb. 27, 1996

[54] HIGH SPEED TOOL SHAFT BEARING SYSTEM

[75] Inventors: Eddy H. Del Rio, Royal Palm Beach; William E. Anspach, Jr., Palm Beach Gardens, both of Fla.

[73] Assignee: The Anspach Effort, Inc., Palm Beach Gardens, Fla.

[21] Appl. No.: 389,059

[22] Filed: Feb. 15, 1995

[51] Int. Cl.⁶ .............................. F16C 19/08; F16C 27/00
[52] U.S. Cl. ........................................... 384/518; 384/535
[58] Field of Search ................................. 384/517, 518, 384/535, 563

[56] References Cited

U.S. PATENT DOCUMENTS

| | | | |
|---|---|---|---|
| 2,511,675 | 6/1950 | Monpain | 384/518 |
| 2,556,368 | 6/1951 | Hegeman | 384/517 |
| 4,668,109 | 5/1987 | Basso | 384/518 |
| 4,719,352 | 1/1988 | Miyatake et al. | 384/517 X |

*Primary Examiner*—Thomas R. Hannon
*Attorney, Agent, or Firm*—Quarles & Brady

[57] ABSTRACT

A bearing system is provide to couple a tool shaft to a power driven surgical instrument that has a support tube with a longitudinally extending aperture for rotation of the tool shaft about an axis. A pair of bearing assemblies are spaced apart within the aperture by a sleeve and a helical spring that axially biases the bearing assemblies within the aperture. Each bearing assembly includes first and second bearings and an interface cartridge. The first bearing has an outer race abutting a flange element in the aperture, and has an inner race. The tubular interface cartridge engages the inner race and has spring elements extending radially into a passage through the interface cartridge to engage the shaft. A second bearing has an inner race abutting the tubular interface cartridge and has an outer race against which force from the spring is applied.

15 Claims, 3 Drawing Sheets

HIGH SPEED TOOL SHAFT BEARING SYSTEM

FIELD OF THE INVENTION

The invention relates to bearing systems for rotational shafts. More particularly, the invention relates to bearing systems for the shafts of surgical tools having rotational speeds in excess of 75,000 RPM.

BACKGROUND OF THE INVENTION

A conventional bearing for radially supporting the shafts of high speed tools, such as pneumatic-motor driven orthopedic and neurosurgical tools, typically includes an inner race mounted to the supported shaft and an outer race mounted to the associated fixed housing. Because of manufacturing tolerances, the path of travel for the roller members,, which interconnect the races, do not define a true circle, even in high precision bearings. In fact, the roller members meander randomly from the ideal circular orbit between the inner and outer races. Also, because of manufacturing tolerances and assembly requirements, there may be play between the outer race and the supporting housing as well as between the inner race and the supported shaft. Consequently, radial motion of the tool shaft is permitted, allowing vibration and chatter. At the high rotational speeds of pneumatically driven surgical tools, such vibrations are unacceptable and in some circumstances can result in catastrophic failure. Accordingly, rotational speeds for such high speed surgical tools have been typically limited to less than 80,000 RPM.

SUMMARY OF THE INVENTION

It is therefore an object of the invention to provide a bearing system for the shafts of high speed systems, such as pneumatically driven surgical tools, that is capable of avoiding catastrophic vibrations at speeds in excess of 80,000 RPM.

It is another object of the invention to provide a bearing system for rotational shafts that minimizes radial shift of the shafts to avoid unacceptable vibration while permitting reasonable manufacturing tolerances in the assembly of the bearing system.

These and other objects of the invention are achieved by a bearing system for high speed rotational shafts that axially preloads the support bearings without preloading the supported shaft. The system comprises a pair of ball bearings each having an outer race fixedly secured to an associated housing or a flange surface of the housing and an inner race axially engaging a shaft interface cartridge that engages and supports the rotating shaft. The interface cartridge and the bearings are axially preloaded to generate a frictional engagement between the abutting faces of the interface cartridge and the inner race. This axial preload compresses the inner and outer races so as to substantially align the sandwiched roller members into a circular path. Additionally, the frictional forces created by the preloaded engagement of the interface cartridge and the inner races of the bearings resist radial motion of the shaft of the supported tool.

The interface cartridge and ball bearing assembly are axially urged together by biasing means, such as a helical spring oriented axially, and slidingly inserted in the housing.

For longer shaft support, a series of bearing assemblies can be provided and share a common biasing means. To transmit the biasing forces to axially separated bearing assemblies, a sliding spacer sleeve can be included in the system. The ends of the entire system can be fixed by stop elements formed by C-clips or other fastening means, for example.

According to another aspect of the invention, the interface cartridge can be constructed to have a series of radially inwardly directed springs that flex to allow insertion of the shaft, but are biased to engage the shaft radially. While other engagement cartridges can be provided within the scope of the invention, an interface cartridge having such radially inwardly directed springs is preferred. In one construction, the radially inwardly directed springs can be formed by wire bands mounted to have pretension radially inwardly.

According to another aspect of the invention, the preferred interface cartridge with radially inwardly biased springs can be constructed by a process that avoids manufacturing difficulties accompanying the insertion of a precut wire spring into the small internal passageway of the cartridge unit. Under this method, the cartridge unit is mounted on a temporary shaft having a diameter that is smaller than the smallest diameter tool shaft to be used with the device in operation. Next, wire used to form the interface spring is inserted from its spool or other source and bent at each axial end of the cartridge so as to extend radially outwardly. The two ends of the wire are then crossed and pulled in tension. Under tension, the wire is snipped adjacent the edges of the cartridge so that the snipped ends fall into notches or other receptacles provided on the cartridge. The temporary shaft is removed, leaving a spring extending radially into the interior of the cartridge passage for biasing engagement by a larger diameter tool shaft.

BRIEF DESCRIPTION OF THE DRAWINGS

A more detailed understanding of the invention can be gained from a reading of the following detailed description in connection with the accompanying drawings, in which.

DETAILED DESCRIPTION OF EMBODIMENTS OF THE INVENTION

The invention relates to a bearing system for radially supporting a high speed rotational shaft. The system has particular application in the support of cutter shafts in surgical tools having rotational speeds in excess of 75,000 RPM. Because the cutter can extend several inches from a connection with the driving motor, a supporting housing, typically referred to as a nose piece, can be provided to shroud the shaft short of its cutting tip and provide a fixed base against which the bearing system can support the traversing shaft. The bearing system of the invention and its various embodiments will be discussed herein in reference to this surgical tool nose piece environment. However, the system can provide similar advantages in other devices having high speed rotational shafts in which minimizing vibrational forces is critical.

Figure 1:
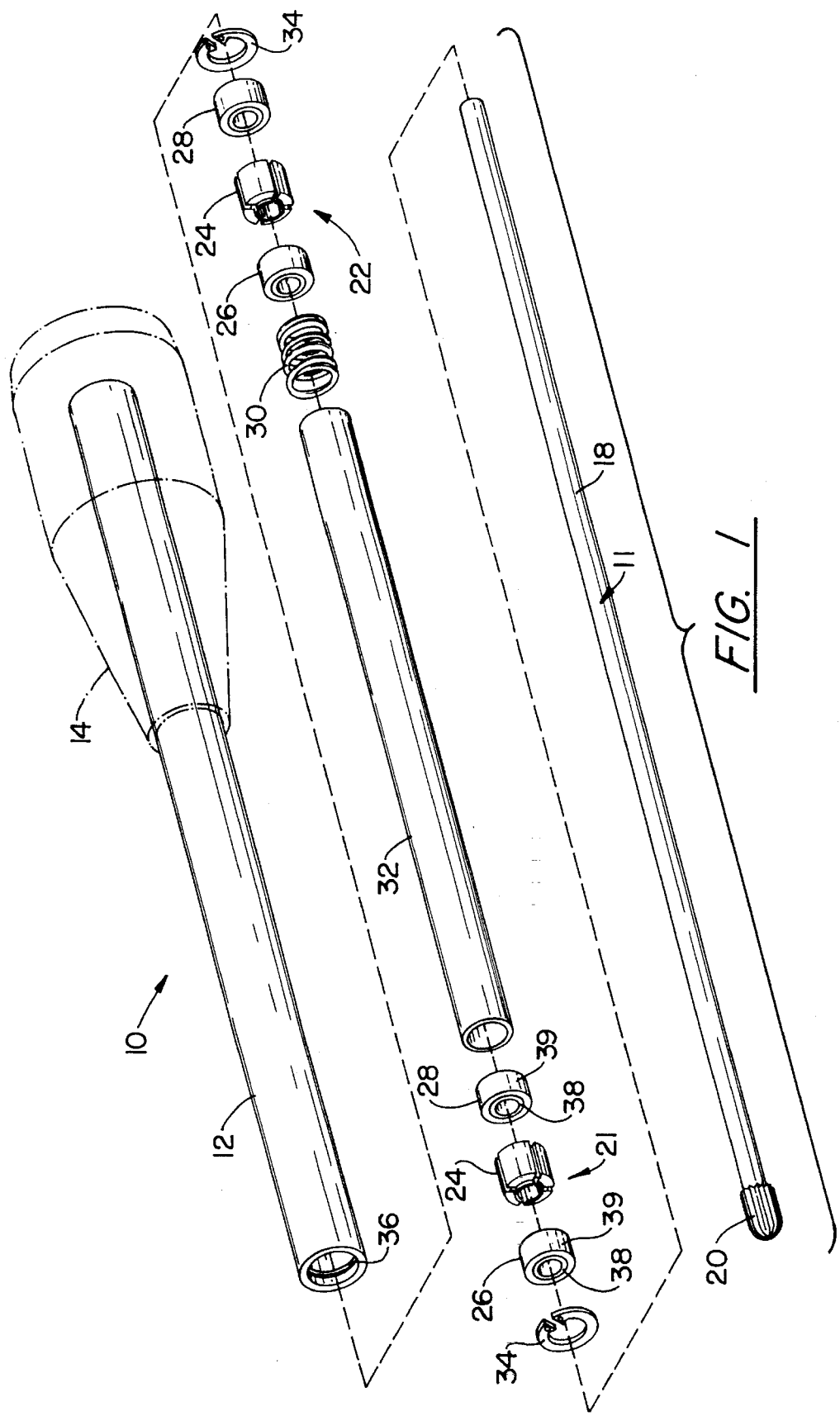
FIG. 1 is an exploded perspective view of an embodiment of the bearing system of the invention as used with a high speed surgical tool.
Figure 2:
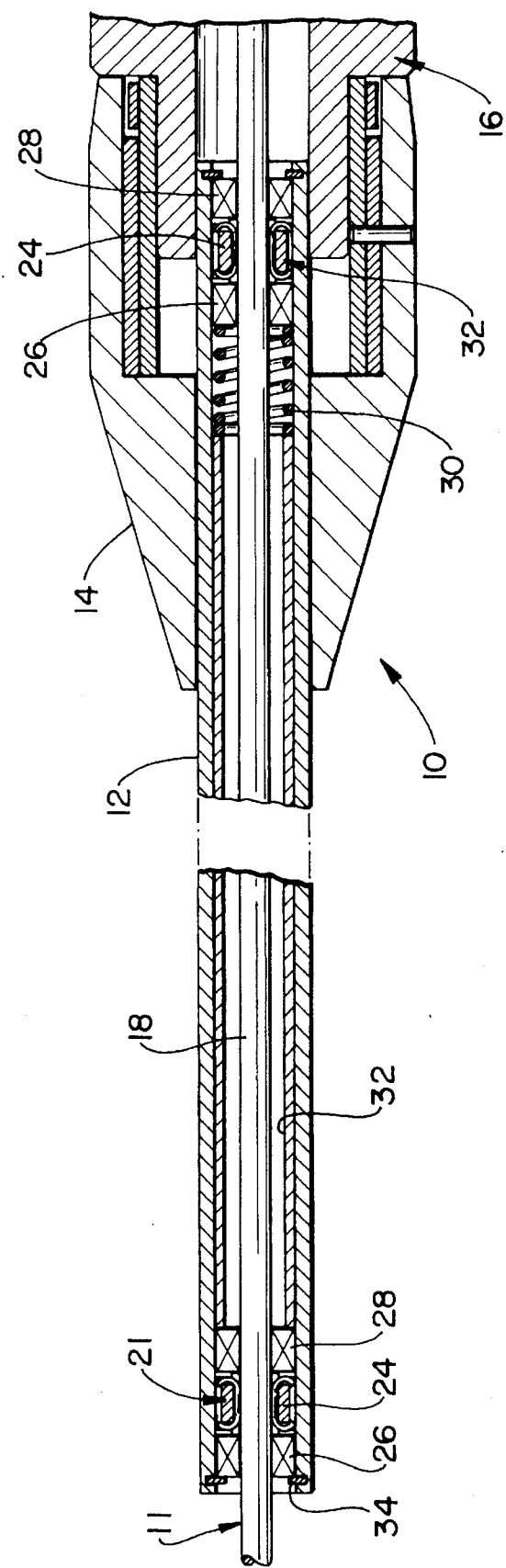
FIG. 2 is a sectional view of an embodiment of the bearing system of the invention as mounted in a nose piece of a surgical tool.

Referring to FIG. 1, the nose piece 10 for a high speed surgical tool 11 includes a tool support tube 12 and a mounting base 14 for connection to a driving source 16, such as a pneumatic motor (see FIG. 2). The tool 11 inserts through the nose piece 10 for connection to the driving source 16. In the embodiment illustrated, the tool shaft 18 is elongated so that it requires two separate bearing assemblies 21 and 22. However, the bearing system is equally applicable to shorter nose pieces in which only a single bearing assembly is necessary.

Each bearing assembly 21 and 22 preferably includes all interface cartridge 24 interposed between axially opposing ball bearings 26 and 28. Biasing means, such as a helical spring 30, is axially positioned to urge the components of the bearing assemblies; 21 and 22 together. The force of the spring 30 is supplied to both bearing assemblies 21 and 22 through a spacer sleeve 32 located axially between the spring 30 and the bearing 28 of the first bearing assembly. The complete bearing system is slidingly disposed within the support tube 12 of the nose piece 10 and is secured at each end of the system by stops, such as C-clips 34 mounted in slots 36 in the support tube. The C-clips provide inner flanges against which the bearings engage and retain the bearing system; alternatively, one of the C-clips could be replaced by a inwardly projecting flange surface machined in the wall of the aperture through the support tube 12.

Each component of the bearing system has a central passage through which the shaft 18 of the tool 11 can pass for insertion through the nose piece 10 and connection of a base end with the driving source 16. The cutting end 20 remains exposed at the opposing end. The cutting end 20 can have a variety of tool end configurations, including a drill or a cutting head.

The bearings 26 and 28 utilized in the bearing system can be any of a multitude of types known in the field so long as each includes an inner race 38 having an axial engagement face rotationally interconnected to an outer race 39. The bearings 26, 28 are preferably ball bearings capable of supporting radial and axial loads. The outer diameter of the outer race 39 is dimensioned to slidingly fit within the support tube 12. The inner diameter of the inner race 38 is dimensioned to allow passage of the tool shaft 18.

Each bearing 26 and 28 is oriented to provide an engagement face of an inner race 38 toward the interface cartridge 24. The interface cartridge 24 also provides a corresponding engagement face, such as a rim, to axially engage the engagement face of each inner race 38.

Referring to FIG. 2, which illustrates the components of the bearing system in cross section as loaded in the support tube 12, the outer diameter of the interface cartridge 24 is dimensioned to ensure a radial clearance, for example 0.005 in., from the support tube 12 when positioned in the support tube 12 and mounted around an inserted shaft. The diameter of the inner passage through nose piece 10 is larger than the largest diameter tool shaft 18 to be inserted in operation, but to insure a positive radial engagement with an inserted shaft, a series of engagement springs, such as wire springs, extend inwardly into the inner diameter and receive an inserted shaft with supporting biased resistance, as will be described.

The helical spring 30 urges the bearings 26 and 28 into preloaded engagement with the interface cartridge 24. The axial preload provides a basis for both radial and circumferential friction forces. The circumferential friction enables the interface cartridge and the inner race to rotate together in connection with the rotating shaft. The radial friction is of course bidirectional, resisting opposing motion both toward the inner passage and a way from it. The radially bidirectional friction resists radial vibrational movement of the shaft. Radial friction is also provided by the preload at the interface of the outer race 39 and the C-clip 34, and this friction provides resistance against the radial vibrational forces.

Figure 3:
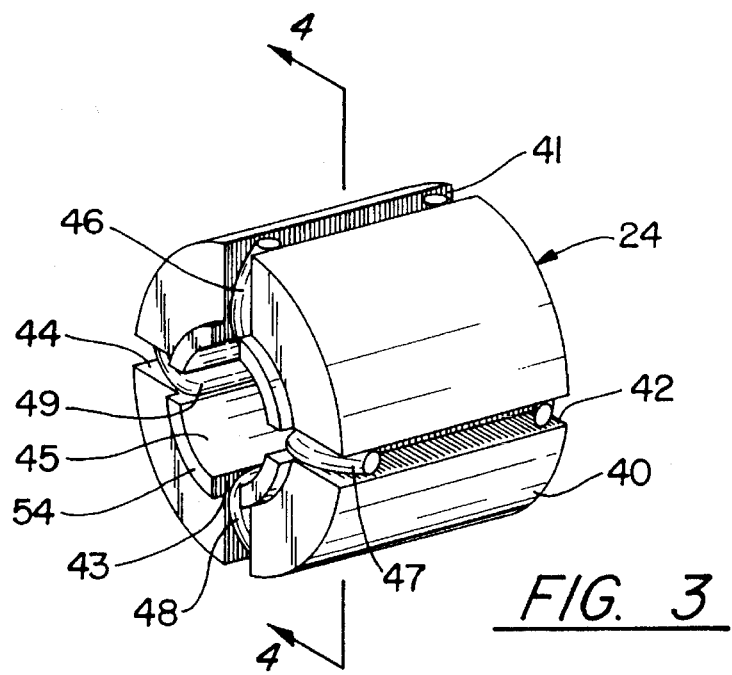
FIG. 3 is a perspective view of an embodiment of a shaft support cartridge utilized in the bearing system of the invention.
Figure 4:
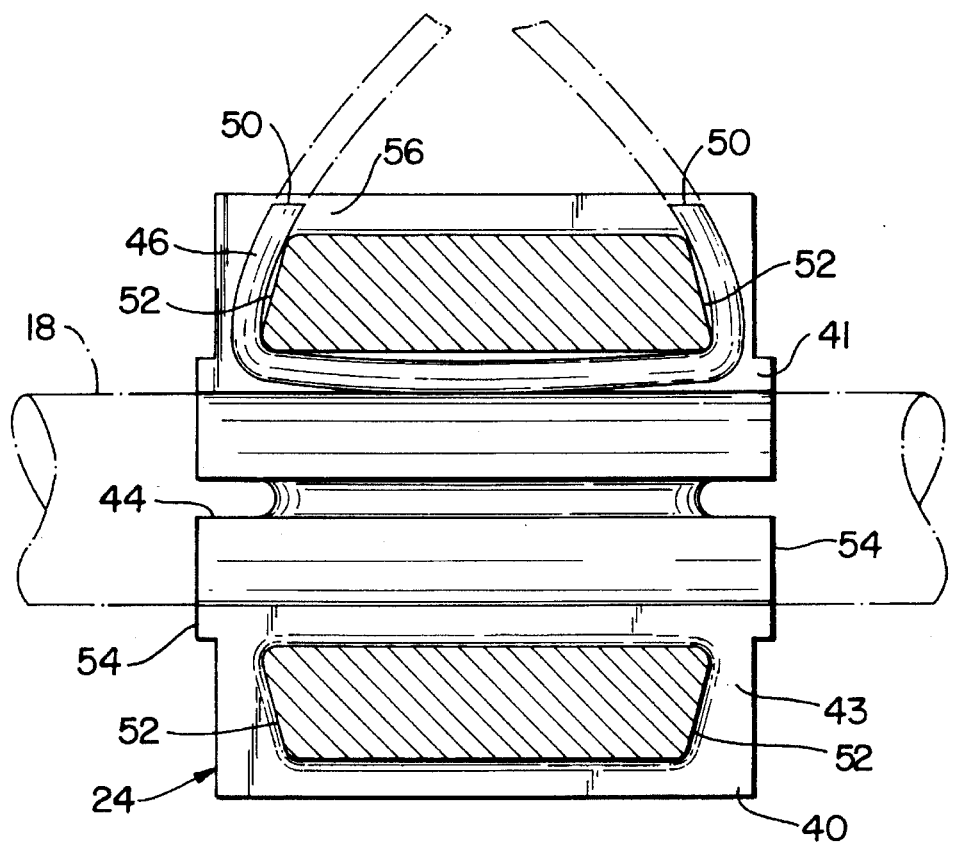
FIG. 4 is a section view taken along 4—4 in FIG. 3.

Referring to FIGS. 3 and 4, the interface cartridge 24 has a preferably cylindrical body 40 with a series of channels 41, 42, 43 and 44, each extending along the inner passage 45, through the ends and along the outer surface to define an encircling channel for one of the wire springs 46, 47, 48 and 49. The interface cartridge 24 can provide two or more channels and wire springs, but preferably provides three or four, as illustrated. The channels 41–44 are preferably equiangularly arranged around the circumference of the interface cartridge 24. The wire springs 46–49 extend inwardly into the inner passage 45 from the channels 41–44 and have ends that hook on angled mounting surfaces 52 within the channels.

Rims 54 extend from opposing ends of the interface cartridge 24 to provide engagement faces with the adjacent inner races 38 of bearings 26 and 28. The rims 54 are dimensioned to avoid contact with the larger diameter outer races 39 so that the high speed rotation of the interface cartridge and the supported shaft 18 is only translated to the inner races.

The wire springs 46–49 urge the tool shaft 18 inwardly and tend to center the shaft thereby. Because the inner passages of the inner races 38 of the bearings 26 and 28 are preferably sized to be spaced from the shaft, the interface cartridge 24 provides the supportive contact with the tool shaft 18 and transfers the supporting forces to the two bearings surrounding the interface cartridge.

Referring particularly to FIG. 4, the wire springs 46–49 provide a biased engagement with the inserted tool shaft 18. Because of the small size of the components, the interface cartridge being, for example, 0.6 cm. in diameter, insertion of premade wire springs into the tiny internal passage 45 and manipulation to attach the ends 50 of the wire spring around the axial slots of channels 41–49 would be difficult and inefficient. Thus, according to another aspect of the invention, a method of making the interface cartridge 24 is provided. To create the wire springs in situ a smaller diameter shaft is temporarily inserted into the inner passage of the interface cartridge 24. According to this method, the cartridge unit is mounted on a temporary shaft having a diameter that is smaller than the smallest diameter tools shaft 18 to be used with the device in operation. Next, wire that is used to form the springs 46–49 is inserted from its spool or other source and bent at each axial end of the interface cartridge 24 so as to extend radially outwardly. The two ends of the wire are then crossed and pulled in tension. Under tension, the wire is snipped adjacent the edges of the cartridge so that the snipped ends 50 fall into notches 56 or other receptacles provided in the channels 41–44 on the cartridge. The temporary shaft is removed, leaving a spring extending radially into the interior of the cartridge passage for biasing engagement by a larger diameter tool shaft.

Referring to FIG. 2, in operation, a shaft 18 of a tool 11 is inserted into the nose piece 10 and through the components of the bearing system. Any off-axis deviation is corrected by the wire springs 46–49 which flex into the interface cartridge channels 41–44 to receive the inserted shaft and grip the shaft with biased resistance. This positive engagement enables the interface cartridge 24 to rotate with the shaft 18 during use. The helical spring 30 urges the interface cartridge 24 against the surrounding bearings 26 and 28. The friction created by the engagement transmits the rotational force to the inner race 38 of the bearings 26 and 28 and resists any radial vibrational forces. The axial preload also aligns the inner and outer races 38 and 39 to improve the performance of the roller members therebetween.

Because of the vibration compensating friction created between various engaging surfaces, the tolerances in the mating of the various component, such as between the outer race 39 and the support tube 32, the inner race 38 and the inserted shaft 18 (which can have varying diameters) and the interface cartridge 24 and the support tube 32 can be somewhat relaxed, along for easier and more economical manufacture.

The foregoing description was primarily directed to preferred embodiments of the invention while some attention was given to various alternatives within the scope of the invention. It is anticipated that one skilled in the art will likely realize additional alternatives that are nw apparent from the disclosure of embodiments of the invention. Accordingly, the scope of the invention should be determined from the following claims and not limited by the above disclosure.

We claim:

1. A bearing system to support a shaft for rotation about all axis in an aperture of a housing, said bearing system comprising:

a first bearing with an outer race abutting a flange surface within the aperture, said first bearing having an inner race;

a second bearing with an inner race and an outer race;

a coupling engaging the inner race of said first bearing and the inner race of said second bearing but not directly contacting the outer race of the first bearing and the outer race of the second bearing; and a spring applying force against the outer race of the second bearing to bias said first bearing, said coupling and said second bearing axially within the aperture against the flange surface.

2. The bearing system as recited in claim 1, wherein said coupling includes a first interface cartridge having a first end engaging the inner race of said first bearing and a second end engaging the inner race of said second bearing, said first interface cartridge bearing a first passage extending between the first end and the second end for receiving a shaft to be supported, said first interface cartridge including spring elements extending radially into the first passage to engage the shaft when inserted.

3. The bearing system as recited in claim 2 wherein said first interface cartridge comprises:

a tubular body through which the first passage is formed, and having a plurality of channels extending axially along the first passage; and a separate wire spring positioned in each of at least two of the plurality of channels and extending radially into the first passage.

4. The bearing system as recited in claim 3 wherein the plurality of channels are equidistantly spaced around the passage in the tubular body.

5. The bearing system as recited in claim 2 further comprising:

a spacer sleeve within the aperture, and having a first end coupled to the outer race of said second bearing, and having a second end;

a third bearing with an outer race coupled to the second end of said spacer sleeve, and having an inner race;

a second interface cartridge engaging the inner race of the third bearing and having a second passage therethrough with other spring elements extending radially into the second passage to engage the shaft;

a fourth bearing with an inner race abutting the second interface cartridge, and having an outer race; and a retainer which is coupled to the outer race of the fourth bearing to hold the fourth bearing within the aperture.

6. The bearing system as recited in claim 5 wherein said spring is positioned between said spacer sleeve and one of said second bearing and said third bearing.

7. The bearing system as recited in claim 5 wherein said aperture of the housing has a slot therein; and said retainer is a C-clip within the slot.

8. The bearing system as recited in claim 5 wherein each of said first interface cartridge and said second interface cartridge comprises:

a tubular body through which is formed one of the first passage and the second passage, and having a plurality of channels extending along that passage; and a separate wire spring positioned in each one of the plurality of channels and extending into the one of the first passage and the second passage.

9. The bearing system as recited in claim 1 wherein the aperture has a slot therein; and further comprising a C-clip within the slot retaining said first bearing, said second bearing and said coupling within the aperture.

10. A bearing system for coupling a shaft of a tool to a power driven surgical instrument for rotation about an axis, said bearing system comprising:

a support tube having an aperture extending longitudinally therethrough for receiving the shaft, and having a flange element extending inwardly into the aperture;

a first bearing assembly within the aperture, and including a first bearing with an outer race abutting said flange element and with an inner race, a first interface cartridge engaging the inner race of the first bearing and having a first passage therethrough with spring elements extending radially into the first passage to engage the shaft, and a second bearing with an inner race abutting the first interface cartridge and with an outer race;

a spring applying force against the outer race of the second bearing to bias said first bearing assembly axially within the aperture and against said flange element.

11. The bearing system as recited in claim 10 wherein said flange element is a C-clip in a slot of the aperture.

12. The bearing system as recited in claim 10 further comprising:

a spacer sleeve within the aperture, and having a first end coupled to the outer race of the second bearing, and having a second end;

a second bearing assembly within the aperture, and including a third bearing with an outer race coupled to the second end of said spacer sleeve and with an inner race, a second interface cartridge engaging the inner race of the third bearing and having a second passage therethrough with spring elements extending radially into the second passage to engage the shaft, and a fourth bearing with an inner race abutting the second interface cartridge and with an outer race; and a retainer coupled to the outer race of the fourth bearing to hold the second bearing assembly within the aperture.

13. The bearing system as recited in claim 12 wherein said retainer is a C-clip in a slot in the aperture.

14. The bearing system as recited in claim 12 wherein each of said first interface cartridge and said second interface cartridge comprises:
- a tubular body through which is formed one of the first passage and the second passage, and having a plurality of channels extending along that passage; and
- a separate wire spring positioned in each one of the plurality of channels and extending into the one of the first passage and the second passage.

15. The bearing system as recited in claim 10 wherein said first interface cartridge comprises:
- a tubular body through which the first passage is formed, and having a plurality of channels each extending along the first passage; and
- a separate wire spring positioned in each one of the plurality of channels and extending into the first passage.

* * * * *

UNITED STATES PATENT AND TRADEMARK OFFICE
CERTIFICATE OF CORRECTION

PATENT NO. : 5,494,359

DATED : February 27, 1996

INVENTOR(S) : Del Rio, et al.

It is certified that error appears in the above-indentified patent and that said Letters Patent is hereby corrected as shown below:

In Column 5, claim 1, line 28, replace "all" with --an--.

Signed and Sealed this

Third Day of September, 1996

Attest:

BRUCE LEHMAN

*Attesting Officer*   *Commissioner of Patents and Trademarks*